United States Patent [19]
Arnold

[11] Patent Number: 5,693,064
[45] Date of Patent: Dec. 2, 1997

[54] DERMAL PUNCH FOR HAIR TRANSPLANTATION AND METHODS

[76] Inventor: James E. Arnold, 24142 Big Basin Way, Saratoga, Calif. 95070

[21] Appl. No.: 375,314

[22] Filed: Jan. 18, 1995

Related U.S. Application Data

[63] Continuation-in-part of Ser. No. 334,655, Nov. 4, 1994, abandoned.

[51] Int. Cl.$^6$ .................................................. A61B 17/16
[52] U.S. Cl. ........................... 606/184; 606/187; 623/15
[58] Field of Search ................................. 606/184, 187; 623/15

[56] References Cited

U.S. PATENT DOCUMENTS

| | | |
|---|---|---|
| 3,522,809 | 8/1970 | Cornell . |
| 3,811,425 | 5/1974 | Widdlefield ................... 3/1 |
| 3,867,942 | 2/1975 | Bellatoni et al. ............ 128/305 |
| 4,122,855 | 10/1978 | Tezel . |
| 4,210,145 | 7/1980 | Nestor et al. ............... 128/305 |
| 4,476,864 | 10/1984 | Tezel ......................... 128/305 |
| 4,961,430 | 10/1990 | Sheahon .................... 606/171 X |
| 5,026,385 | 6/1991 | Schutte et al. .............. 606/167 |
| 5,036,860 | 8/1991 | Leigh et al. ................ 606/171 X |
| 5,060,658 | 10/1991 | Dejter, Jr. et al. . |
| 5,133,360 | 7/1992 | Spears ....................... 606/170 X |
| 5,269,797 | 12/1993 | Bonati et al. ............... 606/184 X |
| 5,269,801 | 12/1993 | Shiau . |
| 5,417,683 | 5/1995 | Shiao ........................... 606/1 |
| 5,439,475 | 8/1995 | Bennett . |

FOREIGN PATENT DOCUMENTS

| | | |
|---|---|---|
| 002666978 A | 3/1992 | France . |
| 1 474 175 | 5/1977 | United Kingdom . |

OTHER PUBLICATIONS premier® Premier Medical Products product brochure entitled "dermal and footcare," p. 3, May 1993.

Charles M. Monell., et al. "The Success or Failure of the Hair Transplant", Arch Otolaryngol, vol. 97, pp. 265–268, Mar. 1973.

Dominic A. Brandy et al., "Utilization of No–Kor Needles for Slit–Micrografting", Elsevier Science Inc., 0148–0812, pp. 336–339, 1994.

Primary Examiner—Michael Buiz
Assistant Examiner—Nancy Mulcare
Attorney, Agent, or Firm—Townsend and Townsend and Crew LLP

[57] ABSTRACT

In one aspect, the invention provides a method for transplanting hair. According to the method, an instrument is provided having a concentric cylindrical shaft having a proximal end, a distal end, and an axis extending therebetween A blade is on the distal end of the shaft normal to the axis of the shaft, and an escape port is provided in the wall of the shaft near the distal end. The instrument is inserted into the skin to a preselected depth where the skin is below the escape port to form a cylindrical incision. The instrument is then removed from the skin. The step of inserting the instrument into the skin is repeated, with any accumulated skin in the shaft being forced through the escape port. In this way, the shaft does not become clogged with tissue after repeated use. A graft of skin having at least one hair is then placed into at least one of the cylindrical incisions.

12 Claims, 10 Drawing Sheets

DERMAL PUNCH FOR HAIR TRANSPLANTATION AND METHODS

CROSS REFERENCE TO RELATED APPLICATIONS

This application is a continuation-in-part application of U.S. patent application Ser. No. 08/334,655, filed on Nov. 4, 1994, now abandoned the complete disclosure of which is herein incorporated by reference.

BACKGROUND OF THE INVENTION

The invention provides a device and method useful in hair transplantation procedures, and in particular to a dermal punch for forming incisions for receiving small grafts of skin having hair.

For many individuals, hair loss can be undesirable or even traumatic. For such individuals, many hair replacement alternatives have been proposed including wigs, hair pieces, and more recently hair transplants. To some individuals, the hair transplant alternative is particularly desirable because living hair can be used to cover bald areas. As methods for hair transplantation continue to improve, this hair replacement alternative is becoming more widely accepted.

In a typical hair transplantation procedure, grafts of skin containing hair are removed from the individual and are transplanted to other areas. To place the grafts into these areas, a number of incisions are made in the scalp. The incisions are then cleaned and a graft is inserted into each incision. When placing the grafts into the incisions, the surgeon attempts to arrange the grafts so that the resulting transplant resembles a normal hairline. To accomplish such a task, it is desirable in some cases to place only a small number of hairs, i.e. 2 to 6, often referred to as a minigraft (or even a single hair, referred to as a micrograft) into the incisions.

Over the years, a variety of techniques have been employed to transplant minigrafts. In one attempt, the use of a dilator has been proposed. According to this method, an 18 or 20 gauge hypodermic needle is employed to form an incision. A dilator is then placed in the incision to dilate the incision. After removal of the dilator, the minigraft is inserted. Over time, the incision shrinks so that the skin will support the graft. However, until the incision shrinks, the graft is unstable and can be displaced. Further, the hypodermic needle contains an angled blade that forms an incision having a variable depth. Such an incision can make it difficult to place a graft of skin into the incision and insure that the graft will remain substantially flush with the scalp.

In another proposed method, a dermal punch has been employed to punch a small diameter hole in the scalp. The graft is then placed in the cylindrical opening left by the punch. Dermal punches are usually formed from a solid piece of stainless steel. The steel is machined to form a cylindrically shaped outer surface, and the distal end is bored to form a cylindrical opening in the punch. The concentric wall of the punch is then sharped at the distal end to provide a blade.

Forming the dermal punch in this manner presents a variety of drawbacks. For instance, machining the punch from a solid piece of stainless steel can be expensive. For this reason, it is often desirable to reuse the punch. However, since hundreds of incisions are formed in a single procedure, the blade can quickly dull requiring the punch to continually be sent to a machinist for resharpening. After a few sharpenings, the punch becomes too short for its intended use requiring disposal of the punch. One particular problem experienced when the blade dulls is that the punch becomes difficult to insert. To overcome this drawback, the punch is often rotated during incision to make penetration of the blade easier. However, the additional step of rotating the punch adds time to the procedure and can therefore be undesirable. Another drawback to machining the punch in this manner is that it usually leaves the walls of the punch thicker than is desirable. A further drawback is that the cylindrical opening is only formed at the distal end. To allow air to be released when forming an incision, a small air hole is usually drilled through the wall of the punch and into the cylindrical opening. This can be problematic in that the cylindrical opening of the punch often fills with tissue and clogs the air hole. The punch then loses its effectiveness until the tissue is removed.

It would therefore be desirable to provide a dermal punch and methods for its manufacture and use that could substantially reduce or eliminate such problems. Such a punch should be relatively inexpensive to manufacture so that it can be disposable if desired. In one aspect, the punch should have a small wall thickness, have a sharp blade, and should be formed so that the distal end near the blade will not easily become clogged with tissue.

SUMMARY OF THE INVENTION

The invention provides a method for forming a dermal punch. According to the method a hypodermic needle is provided having a concentric cylindrical shaft and a sharpened angled distal portion at a distal end of the shaft. The angled distal portion is removed from the shaft to produce a rim at the distal end which is normal to the axis of the shaft. Preferably, a grinding head is rotated and positioned against the shaft to remove the angled distal portion. The rim is then sharpened to provide a concentric blade on the distal end of the shaft.

In an exemplary aspect, the cylindrical shaft includes an inner wall, and the rim is sharpened by reaming the inner wall adjacent the distal end. Alternatively, the rim can be sharpened by grinding an outer wall of the cylindrical shaft. In another aspect, a luer lock is mounted on a proximal end of the shaft. In this way, a handle having a male fitting can be placed into the luer lock. In yet anther aspect, the hypodermic needle is sized to have a gauge in the range from 14 gauge to 22 gauge, usually having an outer diameter in the range from about 0.75 mm to 3 mm, and more preferably having a diameter in the range from about 1 mm to 2.5 mm.

The invention further provides a method for transplanting hair. According to the method, an instrument having a thin-walled concentric cylindrical shaft and a blade on a distal end of the shaft normal to the axis of the shaft is inserted into the skin to a preselected depth. In this way, a cylindrical incision is formed in the skin. Preferably, the thickness of the wall of the shaft will be such that a clean cut can be provided when the blade is inserted into the skin, usually in the range from about 0.2 mm to 0.5 mm. The instrument is then removed from the skin, and a graft of skin having at least one hair is placed into the cylindrical incision.

In one particular aspect, the instrument further includes a luer lock disposed at a proximal end of the shaft. A handle having a male fitting is then inserted into the luer lock prior to inserting the instrument into the skin.

In a particular preferred aspect, the instrument is inserted into the skin without substantial rotation of the shaft. This is accomplished by having the blade sharpened sufficiently such that the punch can be directed into the skin without requiring rotation.

In another aspect, the outer diameter of the blade is varied to vary the diameter of the incision. In still another aspect, a graft of skin having a plurality of hairs is placed into the incision, and in still a further aspect a plurality of incisions are formed in the skin.

In the method, a step is provided for removing tissue from the cylindrical incision formed by the instrument. In another step, the instrument is inserted into the skin with the shaft being substantially perpendicular to the skin at the point of incision.

In still another aspect, the method includes the step of providing suction through the concentric shaft while the shaft is inserted in the skin. Such a step is particularly advantageous in attempting to prevent tissue from being pressed or pushed under the dermis layer when the shaft is inserted into the skin.

The invention provides a dermal punch which includes an elongate concentric cylindrical shaft having a proximal end and a distal end, with the wall of the shaft preferably having a thickness in the range from about 0.2 mm to 0.5 mm. A concentric blade is disposed on the distal end of shaft normal to the axis of the shaft, and a luer lock is attached to the proximal end of the shaft.

Preferably, the shaft is constructed of stainless steel. In another preferable aspect, the proximal end of the shaft is an open. This provides an air hole for relieving air pressure when the punch is inserted into the skin. In still another aspect, a handle is provided having a male fitting disposed in the luer lock. In yet another aspect, the dermal punch includes means for providing suction through the concentric shaft.

A further method is provided for transplanting hair. According to this method, an instrument is provided having a concentric cylindrical shaft having a proximal end, a distal end, and an axis extending therebetween. A blade is on the distal end of the shaft normal to the axis of the shaft, and an escape port is provided in the wall of the shaft near the distal end. The instrument is inserted into the skin to a preselected depth where the skin is below the escape port to form a cylindrical incision. The instrument is then removed from the skin. The step of inserting the instrument into the skin is repeated, with any accumulated skin in the shaft being forced through the escape port. In this way, the shaft does not become clogged with tissue after repeated use. A graft of skin having at least one hair is then placed into at least one of the cylindrical incisions.

In one aspect, the escape port is within about 5 mm to 10 mm of the distal end so that the port will remain above the skin when the shaft is inserted into the scalp. In another aspect, the instrument is grasped between the thumb and at least two fingers.

An alternative embodiment of a dermal punch is provided. The punch includes an elongate concentric cylindrical shaft having a proximal end and a distal end. A blade is provided on the distal end of shaft normal to the axis of the shaft. The shaft includes an aperture near the distal end having a periphery sufficiently large to allow accumulated tissue in the shaft to escape through the aperture when the distal end of the shaft is pressed into the scalp.

In one aspect, the shaft is constructed of carbon steel or stainless steel, and the aperture is positioned about 5 mm or greater from the distal end. In another aspect, the aperture is elliptical in geometry, with a first axis of the ellipse having a length equal to about ninety percent of the inner diameter of the shaft, and a second axis of the ellipse having a length about five times the length of the first axis or greater. In still another aspect, a handle is provided on the proximal end of the shaft, with the handle having a length that is greater than about 3.5 cm, and preferably greater than about 4 cm. Such a length allows the surgeon to grasp the handle between the thumb and at least two fingers.

In one particular aspect, an inwardly extending protrusion is provided on the shaft for engaging tissue directed into the shaft. In this way, tissue directed into the shaft during insertion passes the protrusion. When the shaft is removed from the scalp, the protrusion engages the tissue in the shaft to remove a core of tissue from the scalp. In this way, a cylindrical hole in provided in the scalp which is ready to receive a graft each time the punch is inserted.

The method provides a further method for forming a dermal punch. According to the method, a length of steel tubing is provided. One end of the tubing is ground or reamed to produce a blade on the tubing. A hole is formed in a wall of the tubing near the blade, and the tubing is inserted into a lumen of a handle.

DETAILED DESCRIPTION OF THE SPECIFIC EMBODIMENTS

Figure 1:
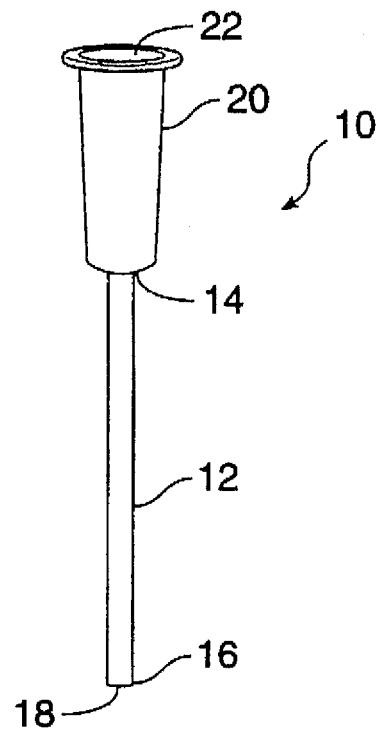
FIG. 1 illustrates a perspective view of an exemplary embodiment of a dermal punch according to the present invention.
Figure 2:
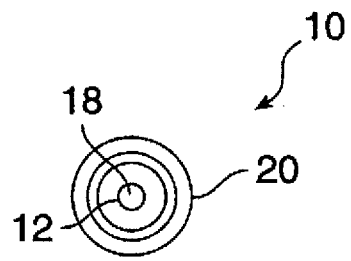
FIG. 2 is a bottom view of the dermal punch of FIG. 1.

Referring to FIGS. 1 and 2, an exemplary embodiment of a dermal punch 10 for forming cylindrical incisions in the skin will be described. The dermal punch 10 is an improvement over the dermal punch described in applicant's copending U.S. patent application Ser. No. 08/298,823, filed Aug. 31, 1994 (Attorney Docket No. 16798-1), the disclosure of which is herein incorporated by reference.

The dermal punch 10 includes an elongate concentric cylindrical shaft 12 having a proximal end 14 and a distal end 16. Preferably, the shaft 12 is constructed of stainless steel. At the distal end 16 is a rim. A concentric blade 18 is formed at the rim and is normal to the axis of the shaft. Preferably, the blade 16 is formed on the inner wall of the shaft (i.e. the wall adjacent the cylindrical opening in the shaft), but can alteratively be formed on the outer wall (i.e. the wall exposed to the environment), or on both the outer wall and the inner wall. The thickness of the wall of the shaft 12 is such that the shaft 12 can easily be depressed into the scalp to provide a clean cut, the thickness preferably being in the range from about 0.2 mm to 0.5 mm. Shafts having such a thickness are found in most commercially available hypodermic needles having gauges in the range from about 14 gauge to 22 gauge.

Attached to the proximal end 14 is a luer lock 20. The luer lock 20 has an open region 22 for receiving a male fitting. The luer lock 20 is preferably attached to the shaft 12 in such a manner so that the proximal end 14 of the shaft 12 is open (similar to luer locks on conventional hypodermic needles). In this way, the entire interior portion of the shaft 12 is in communication with the air from the environment. The luer lock 20 is preferably constructed of a medical grade plastic or polymer.

In one particular aspect, the luer lock 20 is used as a stop to control the depth of blade penetration into the scalp. When configured in such a manner, the length of the shaft 12 will usually be in the range from about 4 mm to 6 mm, and preferably at about 5 mm. Such a length allows the shaft to penetrate through the dermis layer and to the fatty layer of the skin. Alternatively, the depth of blade penetration can be manually controlled. In such a case, the length of the shaft 12 can be much longer and can be varied to the liking of the surgeon.

Figure 3:
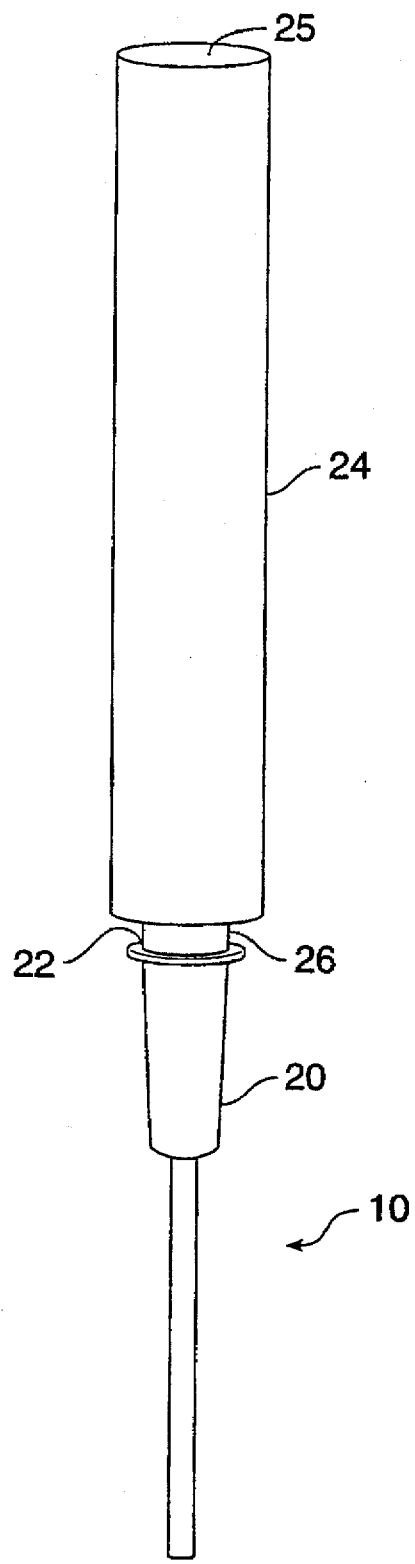
FIG. 3 is a perspective view of the dermal punch of FIG. 1 with a handle attached to a luer lock on the punch.

Referring to FIG. 3, the dermal punch 10 can be provided with a handle 24. The handle 24 includes a male fitting 26 that is received in the open portion 22 of the luer lock 20, usually by a press fit. Alternatively, the male fitting 26 and the open portion 22 can be threaded so that the handle 24 can be screwed into the luer lock 20. In one particular aspect, the handle 24 can be the body of a conventional syringe (approximately 1 cc in size). The handle 24 provides a convenient extension on the punch 10 for easier manipulation of the punch. Preferably, both the male fitting 26 and a proximal end 25 of the handle 24 will be open to the atmosphere so as to provide a vent when the handle 24 is attached to the luer lock 20 and the blade 18 is inserted into skin. Such a configuration helps prevent skin from becoming clogged near the blade 18 during multiple uses. As described in greater detail hereinafter, the open proximal end 25 conveniently allows for suctioning of the surgical site through both the handle 24 and the shaft 12.

Figure 4:
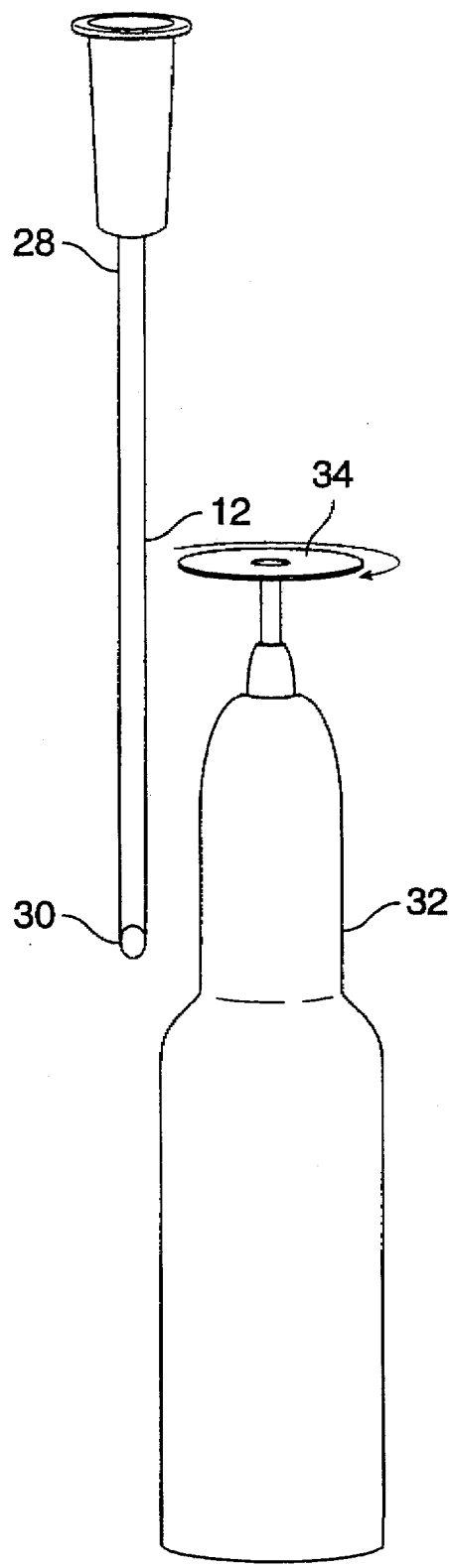
FIGS. 4 and 5 illustrate an exemplary method for forming the dermal punch of FIG. 1.
Figure 5:
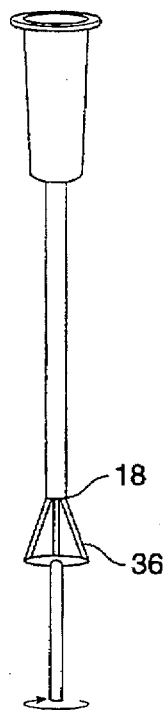

Referring to FIGS. 4–5, an exemplary method for forming the dermal punch 10 illustrated in FIGS. 1 and 2 will be described. The dermal punch 10 will preferably be constructed from a conventional hypodermic needle 28 (see FIG. 4) that is sized to have a gauge in the range from about 14 gauge to 22 gauge. Such needles usually have an outer diameter in the range from about 0.75 mm to 3 mm, and will preferably have an outer diameter in the range from about 1 mm to 2.5 mm. Such needles are available from a variety of commercial suppliers including Beckton Dickinson and Co., Rutherford, N.J. The use of a hypodermic needle in forming the punch is preferable because such needles are relatively inexpensive as compared to punches that are machined from a solid piece of steel. Also, the wall thickness in hypodermic needles is substantially smaller than in machined punches and can provide a cleaner cut into the skin.

The hypodermic needle 28 includes an angled distal portion 30 that is removed to form the rim at the distal end 18. As shown in FIG. 4, a preferred method for removing the angled distal portion is with a powered grinder 32. The grinder 32 has a rotating grinding head 34 that is directed against the shaft 12 at a 90 degree angle relative to the axis of the shaft 12 until the grinding head 34 cuts through the shaft 12. In this way, the grinding head 34 is able to remove the angle distal portion 30 without substantially disfiguring the shaft 12. Alternatively, the angled distal portion 30 can be removed by a variety of other tools and methods, a requirement being that the shaft 12 is not disfigured in the process. Such tools include saws, lathes, pipe cutters, and the like.

To form the concentric blade 18, the inner wall of the shaft 12 is reamed at the distal end 18 as shown in FIG. 5. An exemplary tool for reaming the inner walls of the shaft is a dental burr 36. The dental burr 36 is directed into the interior portion of the shaft 12 and is rotated, preferably by hand, to remove material from the inner wall and form the concentric blade 18. The burr 36 is rotated until the blade 18 is sufficiently sharp so that the blade 18 can penetrate the scalp without rotation. In the event that the blade 18 becomes dull after use, the blade 18 can be resharpened as previously described. Alternatively, since the punch 10 is relatively inexpensive to manufacture, the entire punch 10 can be disposed and a new punch employed.

Alternatively, the blade 18 can be formed on the outer wall by removing material from the outer wall. This is preferably accomplished by placing a grinding head against the outside wall of the shaft 12 at its distal end 18 and rotating the grinding head.

Figure 6:
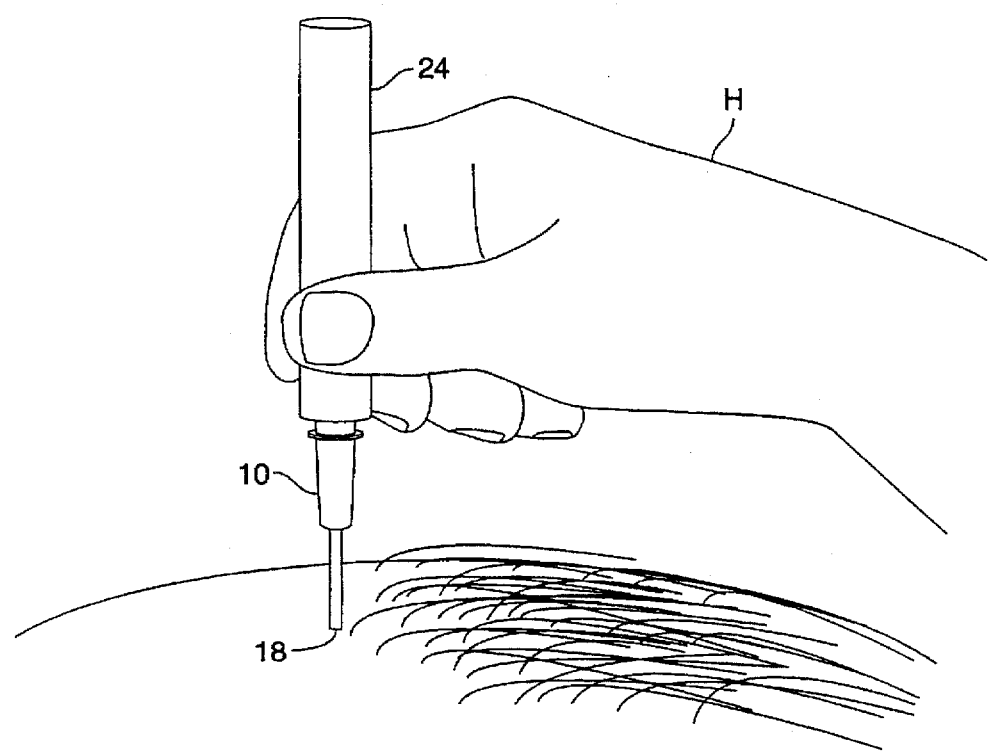
FIGS. 6-9 illustrate an exemplary method for transplanting hair using the dermal punch of FIG. 1.
Figure 7:
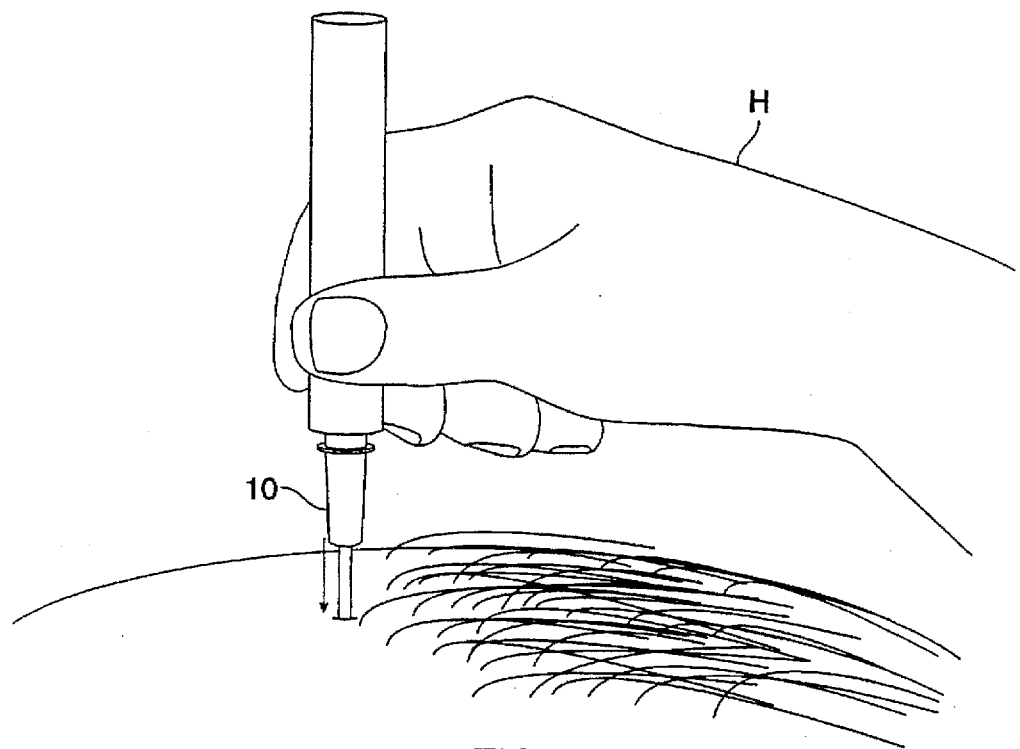
Figure 8:
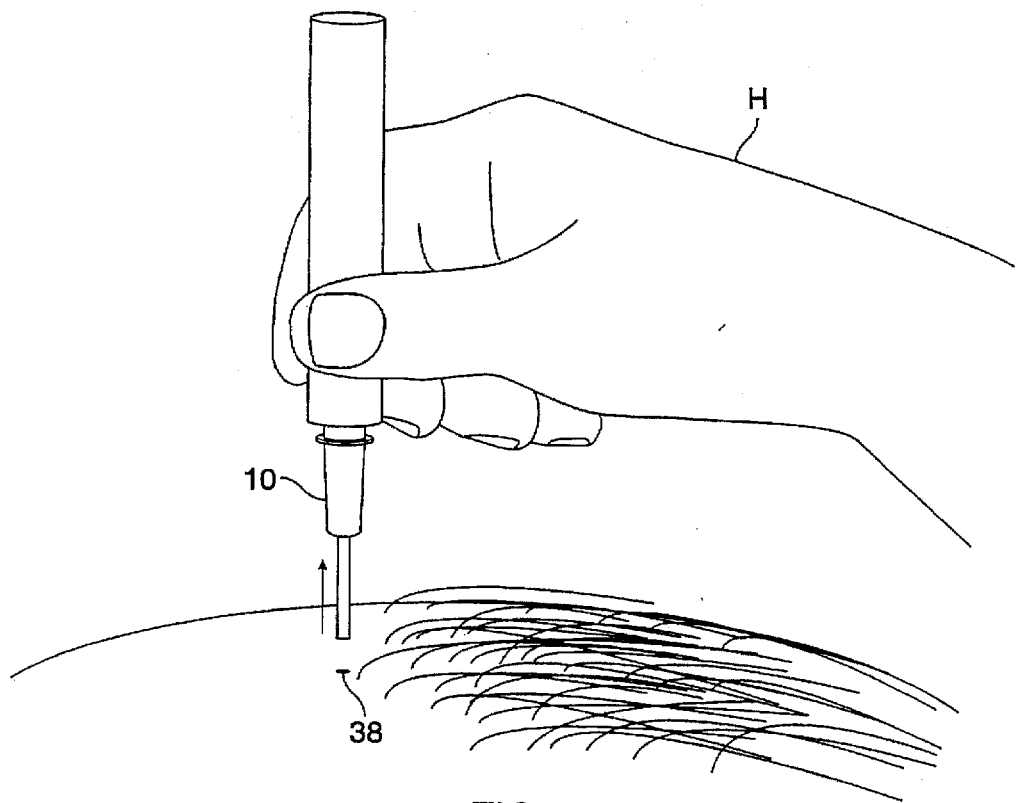
Figure 9:
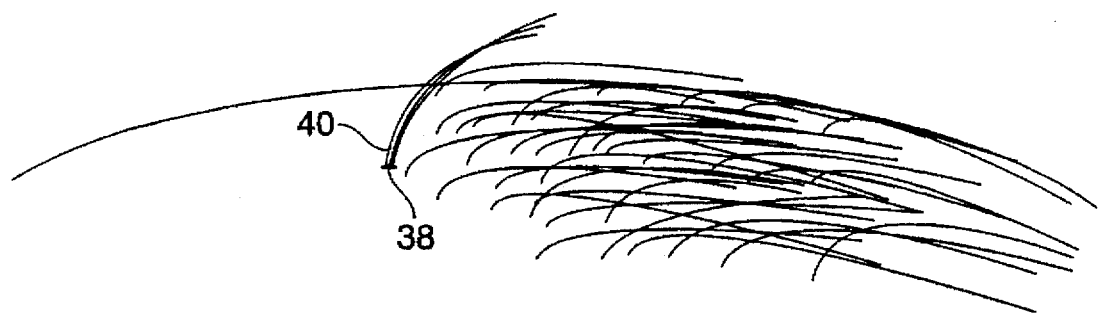

Referring to FIGS. 6–9, an exemplary method for transplanting hair using the dermal punch 10 will next be described. Initially, the handle 24 on the punch 10 is grasped by a hand H and positioned over a patient's scalp as shown in FIG. 6. The shaft 12 is manipulated until the shaft 12 is substantially perpendicular to the patient's scalp at the point of intended incision. The blade 18 is then depressed into the scalp as shown in FIG. 7. Preferably, the blade 18 will be depressed into the scalp without rotation. This allows a plurality of incisions to be formed in a rapid manner. The blade 18 is depressed until penetrating the scalp to a depth of about 5 mm. The blade 18 is then lifted from the scalp to form a cylindrical incision 38 as shown in FIG. 8. If required, any remaining tissue in the cylindrical incision 38 can be removed by tweezers. After the incision 38 is formed, a graft of skin 40 having hair is placed into the incision as shown in FIG. 9.

Figure 10A:
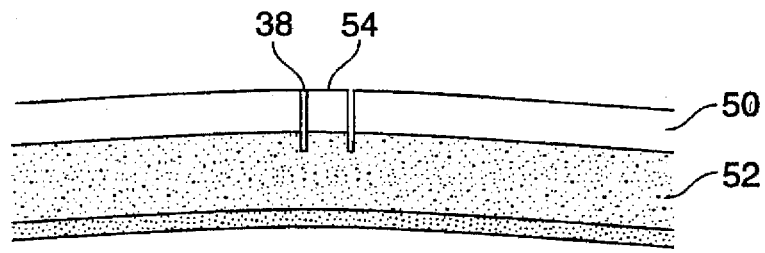
FIG. 10A illustrates a cross-sectional view of the skin showing an exemplary cut using a dermal punch.
Figure 10B:
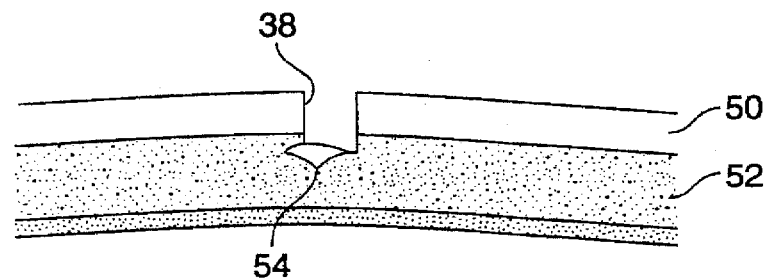
FIG. 10B illustrates the undesirable displacement of tissue into the fatty layer when inserting a dermal punch into the skin.

As shown in FIG. 10A, the cylindrical incision 38 will preferably extend through the dermis layer 50 and into the fatty layer 52, leaving a cylindrical piece of skin 54. Usually, the piece of skin 54 will separate from the fatty layer 52 when the punch 10 is removed from the skin. Sometimes, however, the piece of skin 54 will either remain attached (as shown in FIG. 10A) or it can become lodged under the dermis layer 50 as shown in FIG. 10B. If the piece 54 becomes lodged under the skin, a variety of complications can occur including the formation of a post transplant epidermoid cyst.

Figure 11:
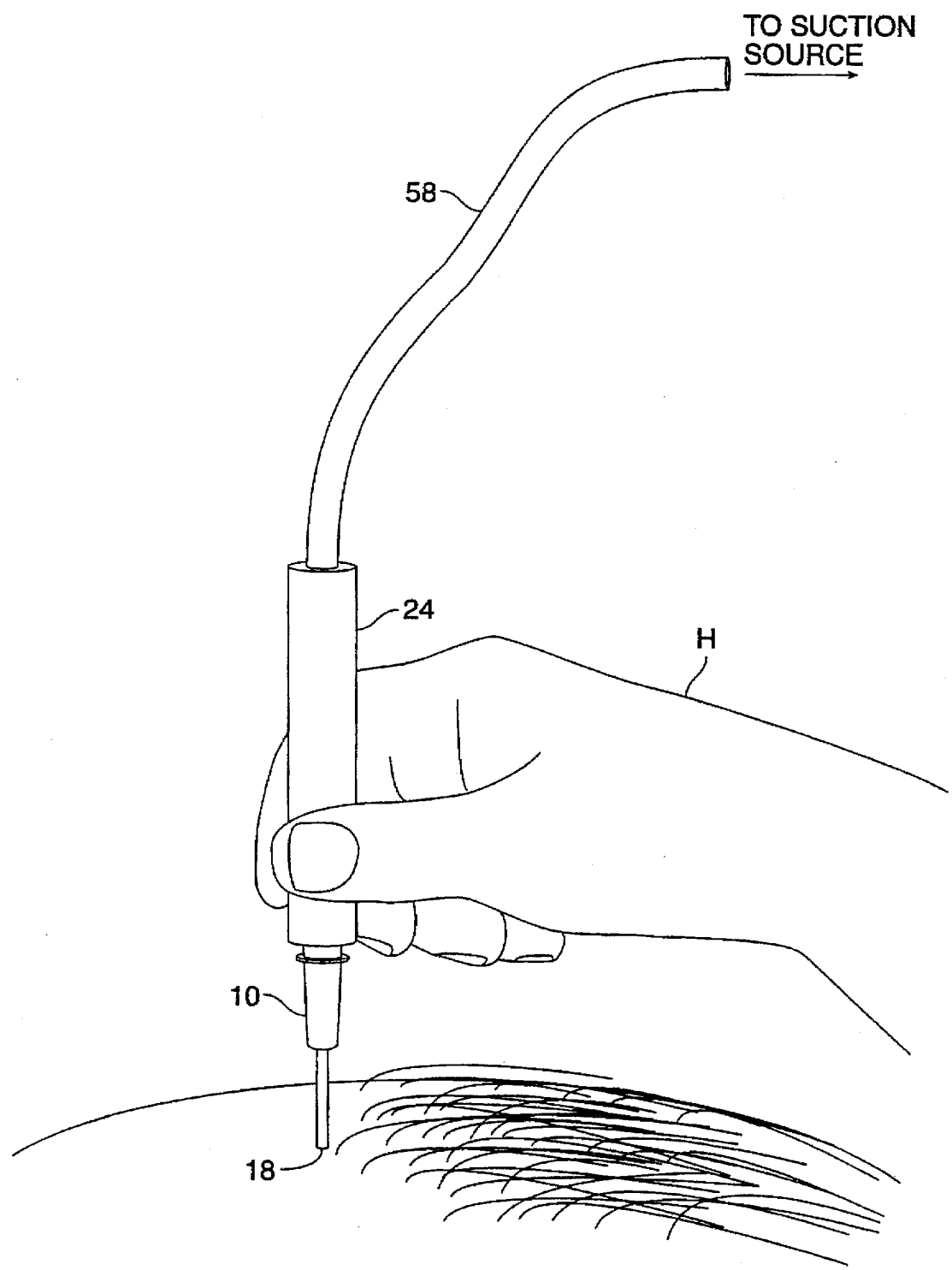
FIG. 11 illustrates an alternative method for inserting the dermal punch of the present invention to help prevent the displacement of tissue into the fatty layer as shown in FIG. 10B.

To help prevent such complications, an alternative method for forming the incision 38 is provided as shown in FIG. 11. According to this alternative method, a suction source (not shown) is provided to the punch 10 via a tube 58. The tube 58 is inserted into or attached to the open proximal end 25 of the handle 24. At its other end, the tube 58 is attached to a suction machine or a house vacuum. In this way, suction is provided through both the handle 24 and the concentric shaft 12. When the shaft 12 is inserted into the scalp, the suction tends to draw the piece of skin 54 into the shaft 12 to help prevent the piece of skin 54 from lodging under the dermis layer. Appropriate filters and collecting apparatus can also be provided to trap and collect any removed skin.

Figure 12:
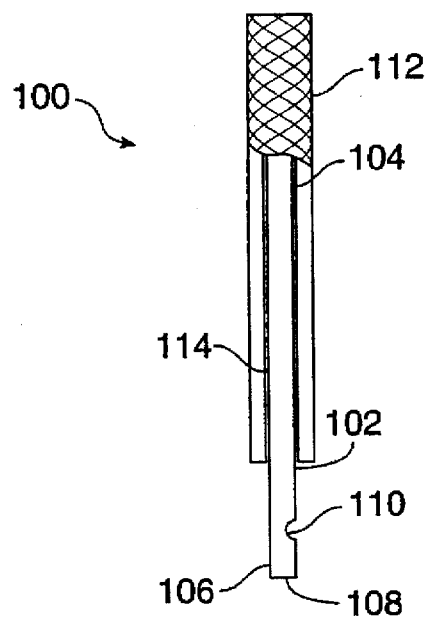
FIG. 12 illustrates an alternative embodiment of a dermal punch according to the present invention.

An alternative embodiment of a dermal punch 100 is illustrated in FIG. 12. The punch 100 includes a concentric cylindrical shaft 102 having a proximal end 104 and a distal end 106. A blade 108 is formed on the distal end 106 and is normal to an axis of the shaft 102 extending between the proximal and distal ends 104, 106. The shaft 102 includes an aperture or escape port 110. As described in greater detail hereinafter, the port 110 in one aspect serves to allow accumulated tissue in the shaft 102 to escape so that the shaft 102 does not become clogged with tissue. In another aspect, the port 110 serves as an air hole to allow air to escape from the shaft 102 when making incisions. The port 102 is provided at a location on the shaft 102 that is sufficiently proximal from the blade 108 so that the port 102 will remain above the skin when the blade 108 is inserted into the scalp. Preferably, the port 110 is located about 5 mm or greater from the blade 108. The port 110 can be provided with a variety of geometries, but needs to be sufficiently large so that accumulated tissue can escape from the shaft 102. The port 110 will preferably be elliptical. In an exemplary configuration, a first axis of the ellipse will have a length that is about ninety percent of the inner diameter of the shaft 102 and a second axis will have a length that is about five times the length of the first axis or greater. Such a configuration is advantageous in allowing accumulated tissue to easily escape from the shaft 102 when forming numerous incisions in the scalp.

The shaft 102 will preferably be constructed from a length of stainless steel tubing that is cut to the proper length. Use of stainless steel tubing is advantageous because of its low cost. Alternatively, the shaft 102 can be constructed of carbon steel tubing. Use of carbon steel is advantageous in that it can easily be sharpened to a degree sufficient so that it can be punched through the skin without rotation when forming incisions.

To form the blade 108, the distal end 106 can be ground, milled, reamed, or the like. In this way, the shaft 102 can easily be resharpened and reused. Reuse of the shaft is desirable in reducing costs of the surgery. To form the port 110 in the shaft 102, the side of the tubing can be milled, ground, or the like.

The punch 100 further includes a handle 112 that is preferably constructed of stainless steel and has a knurled surface. The handle 112 includes a central lumen 114 for receiving the shaft 102. The shaft 102 can be attached to the handle 112 in a variety of way such as by a press fit. In one particularly preferable aspect, the shaft 102 is removably attached to the handle 112 so that the shaft 102 can be replaced. Replacement of the shaft 102 is often necessary after several sharpenings which reduce the length of the shaft 102. By having a reusable handle, the shaft 102 can be sold as a deposable item. An exemplary handle that is reusable with different shafts is described in co-pending U.S. patent application Ser. No. 08/375,312 (Attorney Docket No. 16798-1-1), filed on the same date as the present application, the disclosure of which is herein incorporated by reference.

Figure 13:
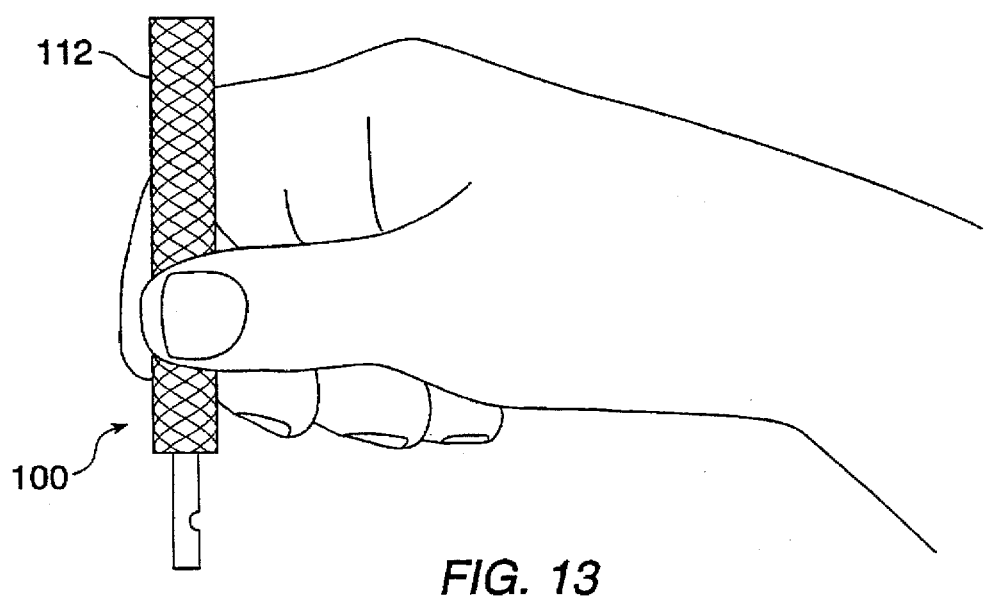
FIG. 13 illustrates an exemplary method for grasping the punch of FIG. 12.

The handle 112 preferably has a length sufficiently long so that the handle 112 can be grasped between the thumb and at least two fingers as shown in FIG. 13. Preferably, the handle 112 will have a length that is greater than or equal to about 4 cm. Such a length is longer than existing dermal punches which are designed to be grasped between the thumb and the index finger only so that the punches can be rolled between the thumb and the index finger during insertion. However, such a grip easily fatigues the surgeon's hand when making multiple incisions. The handle 112 of this invention allows for the punch 100 to be grasped between the thumb and at least two fingers to reduce the problems of fatigue. The blade 108 on the punch 100 is made sufficiently sharp so that rotation of the blade 108 is not needed when making incisions, thereby further reducing fatigue and operation time. Grasping of the handle 112 in this way is further advantageous in providing stability to the punch 100 and allows for easier orientation when pressing the blade 108 into the scalp. The handle 112 preferably has a diameter that is equal to or greater than about 3/16 inch to provide for a more comfortable grip.

Figure 14:
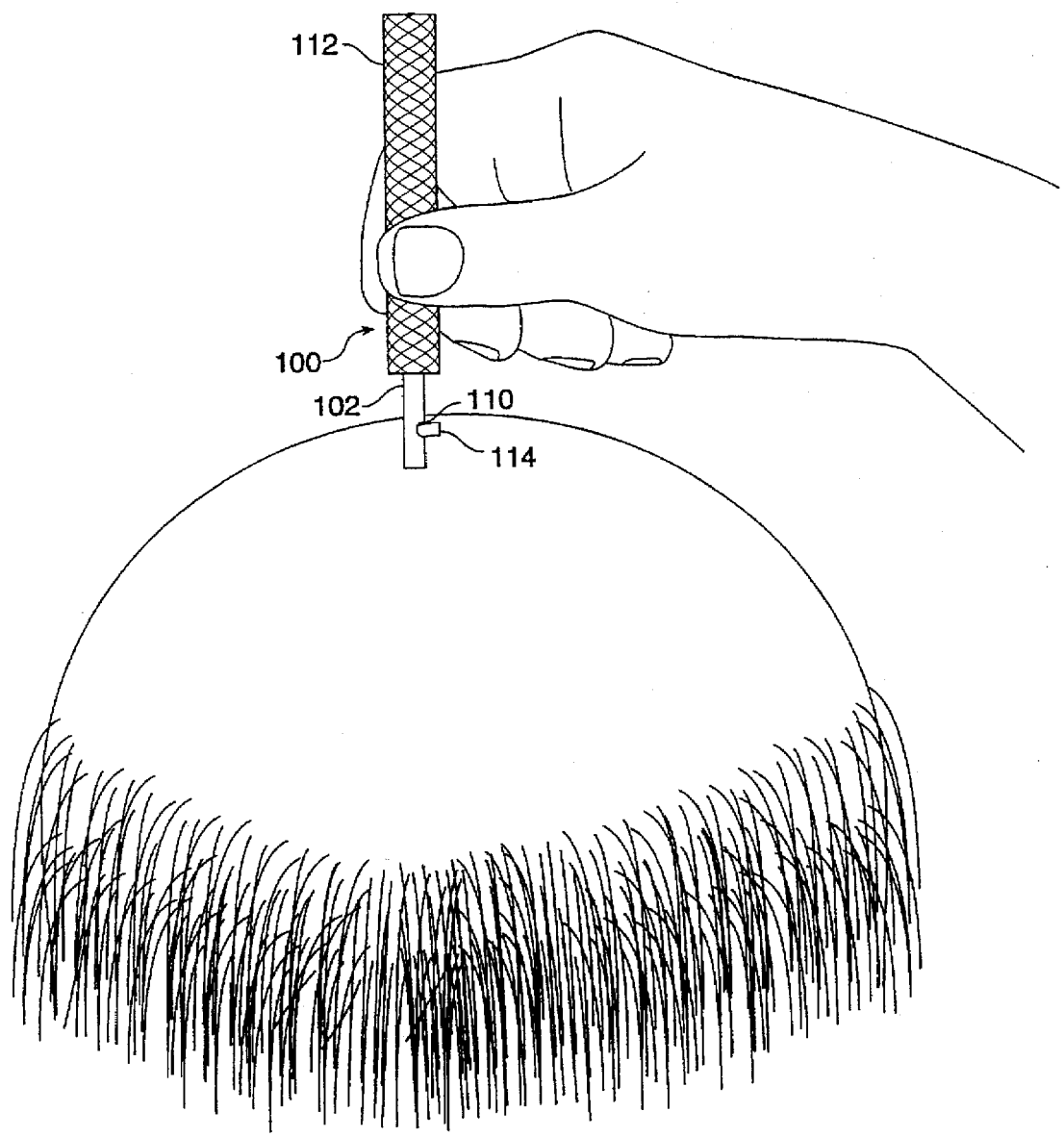
FIG. 14 illustrates an exemplary method for using the punch of FIG. 12 in a hair transplantation procedure.

An exemplary method for using the punch 100 in a transplantation procedure is shown in FIG. 14. The handle 112 of the punch 100 is grasped as previous described in FIG. 13. The blade 108 is then pressed into the scalp with the blade 108 being normal to the scalp. The blade 108 is preferably inserted without rotation. The blade 108 is then removed from the scalp to form a cylindrical incision. Another incision is then formed in the same manner. As more incisions are made, cylindrical plugs of tissue 114 from the scalp usually separate from the scalp and accumulate in the shaft 102. In a typical procedure, scores of incisions are made. If the accumulate tissue is not removed, the punch 100 can become clogged and will be inoperable. In the method of the invention, such tissue is removed from the shaft during use of the punch 100. As the shaft 102 is pressed into the scalp, the accumulated tissue is forced through the shaft 102 where it escapes through the port 110. In this way, a number of incisions can be made without having the shaft 102 becoming clogged with tissue. This saves time for the surgeon who can continuously form incisions without having to slop and clear any tissue from the shaft 102 or obtain a new punch.

The dermal punch of the invention can be provided with a protrusion that extends into the interior of the shaft. The protrusion is fashioned such that tissue can pass the protrusion when the punch is inserted into the scalp, but is prevented from passing back past the protrusion when the punch is removed. In this way, the cylindrical core of tissue formed by the punch is removed each time the punch is inserted. This eliminates the step of separately removing the core of tissue from the scalp after removing the punch. The protrusion is provided at or below the tissue escape port so that the removed tissue is still able to be removed from the shaft as previously described.

Figure 15:
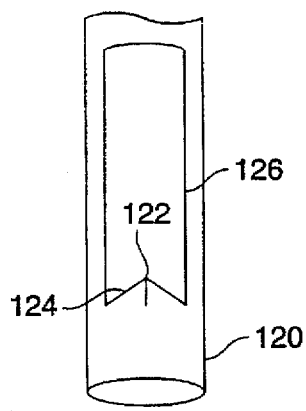
FIG. 15 illustrates a concentric cylindrical shaft of a dermal punch having an inwardly extending protrusion for engaging tissue in the shaft.
Figure 16:
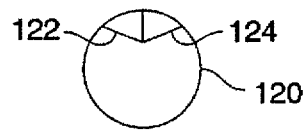
FIG. 16 is a bottom view of the shaft of FIG. 15.
Figure 17:
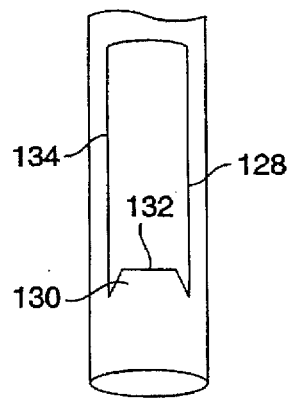
FIG. 17 illustrates an alternative embodiment of a concentric cylindrical shaft of a dermal punch having an inwardly extending protrusion for engaging tissue in the shaft.
Figure 18:
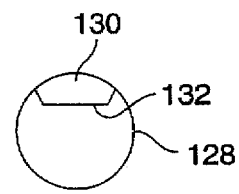
FIG. 18 is a bottom view of the shaft of FIG. 17.

An exemplary shaft 120 having a protrusion 122 is shown in FIGS. 15 and 16. The protrusion 122 is formed by crimping the shaft 120 at a lower edge 124 of an escape port 126. An alternative shaft 128 is shown in FIGS. 17 and 18. The shaft 128 has a lip or protrusion 130 that is formed at a lower edge 132 of an escape port 134. The protrusions 122 and 130 are formed such that tissue can pass by them only in the direction of the escape ports 126, 134. In this way, tissue which has passed the protrusions 122, 130 becomes engaged with the protrusions 122, 130 when the shafts 120, 128 are removed from the scalp. Further removal of the shafts 120, 128 separates the tissue from the scalp.

Although the foregoing invention has been described in detail by way of illustration and example, for purposes of clarity of understanding, it will be obvious that certain changes and modifications may be practiced within the scope of the appended claims.

What is claimed is:

1. A method for transplanting hair, comprising:

inserting an instrument having a cylindrical shaft and a blade on a distal end of the shaft normal to the axis of the shaft into the skin to a preselected depth to form a cylindrical incision, wherein the shaft has an outer diameter in the range from about 0.75 mm to about 3 mm and the thickness of the wall of the shaft is in the range from about 0.2 mm to 0.5 mm, wherein the instrument is inserted into the skin without substantial rotation of the shaft;

removing the instrument from the skin; and placing a graft of skin having at least one hair into the cylindrical incision.

2. The method of claim 1, wherein the instrument further includes a luer lock disposed at a proximal end of the shaft, and wherein a handle having a male fitting is inserted into the luer lock prior to inserting the instrument into the skin.

3. The method of claim 2, further comprising forming a plurality of incisions in the skin and placing a graft of skin having hair into at least one of the incisions.

4. The method of claim 1, further comprising removing tissue from the cylindrical incision formed by the instrument.

5. The method of claim 1, wherein the instrument is inserted into the skin with the shaft being substantially perpendicular to the skin at the point of incision.

6. The method of claim 1, further comprising providing suction through the concentric shaft while inserting the instrument into the skin.

7. A method for transplanting hair, comprising:

providing an instrument having a cylindrical shaft having a proximal end, a distal end, and an axis extending therebetween, wherein a blade is on a distal end of the shaft normal to the axis of the shaft, and wherein an escape port is in the wall of the shaft near the distal end, wherein the escape port is sized sufficient to allow tissue cut by the blade to pass therethrough; wherein the escape port is elliptical in geometry, wherein a first axis of the ellipse has a length equal to about ninety percent of the inner diameter of the shaft, and wherein a second axis of the ellipse has a length about five times the length of the first axis or greater;

inserting the instrument into the skin to a preselected depth where the skin is below the escape port to form a cylindrical incision;

removing the instrument from the skin;

repeating the step of inserting the instrument into the skin while allowing accumulated skin in the shaft to be forced through the escape port; and placing a graft of skin having at least one hair into at least one of the cylindrical incisions.

8. The method of claim 7, wherein the escape port is within about 5 mm to 10 mm of the distal end.

9. The method of claim 7, further comprising grasping the instrument between the thumb and at least two fingers.

10. The method of claim 7, further comprising an inwardly extending protrusion on the shaft, wherein the protrusion channels accumulated tissue within the shaft through the escape port.

11. A method for transplanting hair, comprising:

inserting an instrument having a cylindrical shaft and a blade on a distal end of the shaft normal to the axis of the shaft into the skin to a preselected depth to form a cylindrical incision, wherein the shaft has an outer diameter in the range from about 1 mm to about 2 mm and the thickness of the wall of the shaft is in the range from about 0.2 mm to 0.5 mm;

removing the instrument from the skin; and placing a graft of skin having at least one hair into the cylindrical incision.

12. The method of claim 11, wherein the shaft includes an escape port in the wall of the shaft near the distal end, wherein the escape port is sized sufficient to allow tissue cut by the blade to pass therethrough; and further comprising repeating the step of inserting the instrument into the skin while allowing accumulated skin in the shaft to be forced through the escape port.

* * * * *